United States Patent [19]

Christian et al.

[11] Patent Number: 5,267,791
[45] Date of Patent: Dec. 7, 1993

[54] SUSPENDED CELL CULTURE STIRRING VESSEL CLOSURE AND APPARATUS

[75] Inventors: Stephen R. Christian, Painted Post; Dennis M. O'Connell, Corning, both of N.Y.

[73] Assignee: Corning Incorporated, Corning, N.Y.

[21] Appl. No.: 807,156

[22] Filed: Dec. 13, 1991

[51] Int. Cl.⁵ .............................................. B01F 7/00
[52] U.S. Cl. ................................. 366/249; 366/245; 366/247; 366/273; 422/102; 435/284; 435/286; 435/287; 435/296; 435/312; 435/316; 220/254; 220/361; 220/367; 215/309
[58] Field of Search .............. 435/284, 286, 287, 296, 435/316, 312, 315; 422/99, 102; 366/273, 247, 245, 249; 220/254, 361, 367, 369; 215/309

[56] References Cited

U.S. PATENT DOCUMENTS

| | | | |
|---|---|---|---|
| 2,958,517 | 11/1960 | Harker et al. | 366/273 X |
| 3,468,520 | 9/1969 | Duryea et al. | 366/191 |
| 3,572,651 | 3/1971 | Harker | 366/273 X |
| 3,622,129 | 11/1971 | Mazowski | 366/247 |
| 3,649,465 | 3/1972 | Scharf et al. | 435/284 |
| 3,854,704 | 12/1974 | Balas | 366/274 |
| 3,900,186 | 8/1975 | Balas | 366/273 |
| 4,032,118 | 6/1977 | Phillips | 366/251 |
| 4,153,173 | 5/1979 | Ward et al. | 215/309 X |
| 4,289,854 | 9/1981 | Tolbert et al. | 435/241 |
| 4,355,906 | 10/1982 | Ono | 366/274 |
| 4,382,685 | 5/1983 | Pearson | 435/316 X |
| 4,465,377 | 8/1984 | de Bruyne | 366/273 |
| 4,483,623 | 11/1984 | Eaton et al. | 366/247 |
| 4,498,785 | 2/1985 | de Bruyne | 366/274 |
| 4,508,455 | 4/1985 | Lerman et al. | 366/247 |
| 4,512,666 | 4/1985 | O'Connell | 366/249 |
| 4,649,118 | 3/1987 | Anderson | 435/316 |
| 5,047,347 | 9/1991 | Cline | 435/284 X |
| 5,167,449 | 12/1992 | Killough | 366/247 |

FOREIGN PATENT DOCUMENTS

| | | |
|---|---|---|
| 3904848 | 8/1990 | Fed. Rep. of Germany . |
| 2053704 | 2/1981 | United Kingdom . |
| 2054397 | 2/1981 | United Kingdom . |
| 2062481 | 5/1981 | United Kingdom . |

OTHER PUBLICATIONS

The Corning Laboratory Catalog, 1988, p. 159.
Techne MCS-104 Brochure, 1983.

*Primary Examiner*—Jill A. Johnston
*Assistant Examiner*—Maureen M. Wallenhorst
*Attorney, Agent, or Firm*—Brian R. Leslie; Stephen R. Christian

[57] ABSTRACT

The present invention relates generally to laboratory apparatus and more particularly to disposable suspended magnetic stirrers. An apparatus having a stirring vessel closure and a stirring vessel is disclosed. The stirring vessel closure includes a suspended magnetic impeller, the elevation of which is adjustable by a moveable bearing. The invention is particularly suitable for applications in which solids must be suspended in a liquid medium with a minimum of shear forces, such as in the suspension of tissue cell cultures in a growing medium. The disclosed stirring vessel closure has inclined access ports to allow improved pipette accessibility to the interior of the stirring vessel while also providing improved close packing of stirring vessels during usage or storage.

20 Claims, 3 Drawing Sheets

SUSPENDED CELL CULTURE STIRRING VESSEL CLOSURE AND APPARATUS

FIELD OF THE INVENTION

The invention relates to a cell culture stirring vessel closure and apparatus. More particularly, a stirring vessel closure having an elevation-adjustable suspended magnetic paddle assembly is disclosed. The invention is particularly suitable for use in applications where solids are to be suspended in a liquid medium with minimal shear forces, such as required when suspending tissue or cell cultures in a growing medium.

BACKGROUND OF THE INVENTION

Currently, there are a variety of magnetic stirrers used for suspending biological cells, or tissue growths, in a liquid growing medium. These stirrers typically include a vessel and a closure having a stirring member, or paddle assembly, consisting of a magnet that spins about a vertical axis upon subjecting the stirring assembly to a rotating magnetic field. The stirring assembly may also include paddles that are designed to stir the cell culture at relative slow speeds to avoid damaging the cells as they are being mixed into the growing medium.

U.S. Pat. No. 4,512,666 discloses a prior art adjustable-height magnetic stirrer having a suspended magnetic impeller that is vertically adjustable by rotating a threaded sleeve member disposed within a threaded support member. By rotating the threaded sleeve member, the magnetic impeller rises up or down, depending on the direction of rotation, due to it being attached to a bearing surface at the end of the threaded sleeve member.

U.S. Pat. No. 4,512,666 also discloses a vessel having access ports extending outwardly from the side walls of the vessel at an angle to allow pipettes or other instruments to be inserted into the vessel to gain access to cultures therein. U.S. Pat. No. 4,512,666 further discloses a closure having a gas permeable membrane allowing for the exchange of gases to the ambient while minimizing the risk of contaminating the cell culture within the vessel.

Shortcomings with prior art apparatus, including the apparatus disclosed in U.S. Pat. No. 4,512,666, is that specially designed vessels having access ports must be obtained and used if quick and convenient access to the cell culture contained therein is to be achieved. Additionally, such access ports may provide only a limited amount of access to certain areas of the interior of the vessel due to the stirring member, or paddle assembly, blocking the port. Therefore, it may be necessary to remove the closure to reach those areas thereby increasing the chances of contaminating the culture contained therein.

A further shortcoming with stirring vessels having access ports protruding from the sides thereof, is the ports often interfere with each other when packing the vessels closely together for storage. The ports also interfere with each other when placed close to each other on magnetic stirring plates large enough to accommodate several vessels simultaneously.

Furthermore, such vessels having access ports are relatively expensive due to their inherent construction costs. Expenses can be compounded if the vessels must be replaced due to being broken during usage or storage.

OBJECTS OF THE INVENTION

An object of this invention is to provide a magnetic stirring vessel closure that can be used with a variety of stirring vessels, including vessels that do not have access ports.

Another object of this invention is to provide a magnetic stirring apparatus that is relatively inexpensive.

Another object of this invention is to provide a stirring apparatus that can be disposed of after one usage, or that may be sterilized in whole, or in part, for multiple usages.

A further object of this invention is to provide a stirring vessel closure that may include a gas permeable membrane therein for gas exchange between the interior of the stirring vessel and the ambient.

A yet further object of this invention is to provide a stirring vessel closure that has an optimized relative volume with respect to the ratio of the volume of air to the volume of growing medium contained within the stirring vessel and the closure as a whole.

An additional object of this invention is to provide a high degree of pipette, or other instrument, accessibility to the interior of the stirring vessel.

These and other objects are achieved by the invention disclosed within the drawings and the descriptions herein.

SUMMARY OF THE INVENTION

A magnetic stirring vessel closure having an elevation-adjustable paddle assembly is provided. The closure is specifically provided with a closure body having a circular, centrally located, and substantially horizontal facing having an aperture surrounded by a hollow and internally threaded elevation screw hub extending upward from the horizontal facing. The closure body is further provided with an annular, intermediately located, and sloped facing connecting the horizontal facing to an outwardly located annular facing, the outwardly located annular facing having a peripheral skirt portion extending substantially vertically downward therefrom. The peripheral skirt portion also has means to couple with stirring vessels. The sloped intermediate facing has at least one open-ended, outwardly extending access port surrounding an aperture in the sloped intermediate facing. The horizontal facing includes an externally threaded elevation screw sized and configured to be threadingly received by the elevation screw hub. The elevation screw has a downwardly extending shaft terminating into an outwardly flared lower end sized to pass through the screw hub. The flared lower end of the elevation screw is configured to provide an annular bearing surface for the paddle assembly. The remaining end of the elevation screw has an outwardly flared upper end sized and configured to engage an elevation screw cap.

A paddle assembly having a plurality of combinable hollow sleeves is disclosed. The sleeves, when combined, form a magnet retaining end. The sleeves have a plurality of vertically extending members. The vertical members terminate into a multiple piece bearing surface configured to encompass and ride about the lower bearing surface of the elevation screw. One or more of the hollow sleeves have a paddle extending outwardly therefrom. Securing means for releasably securing the paddle assembly together is provided.

A compatible stirring vessel having a dimple and a trough located about the periphery is further provided.

An alternative embodiment of the stirring vessel closure having a substantially horizontal closure body in lieu of a generally conically shaped closure body having a sloped intermediate facing is additionally disclosed.

DETAILED DESCRIPTION OF THE DRAWINGS

Figure 1:
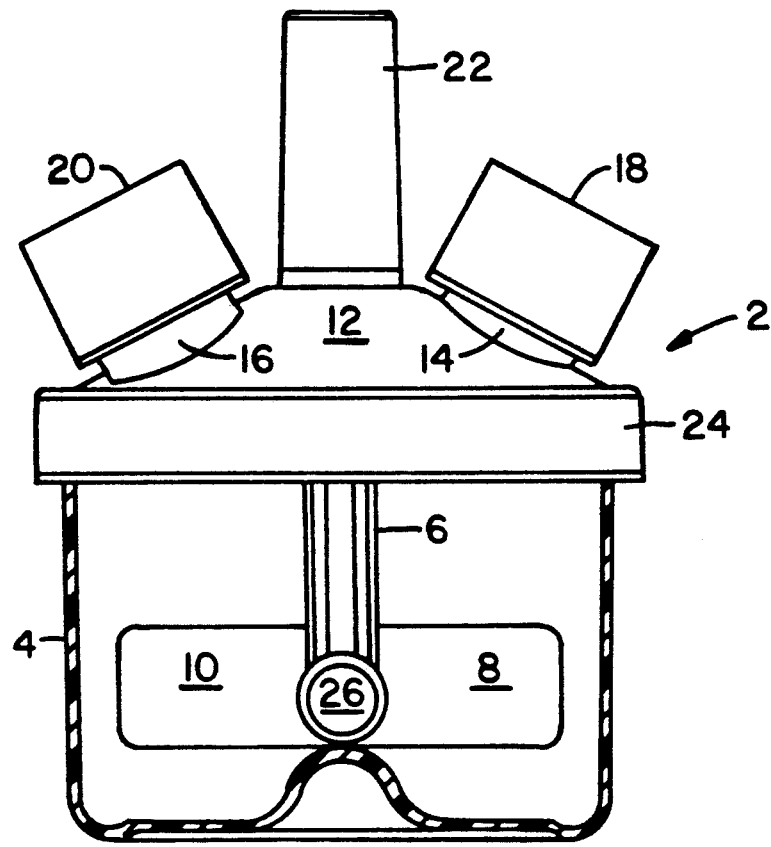
FIG. 1 is a side view of an embodiment of the disclosed magnetic stirring vessel closure having an elevation-adjustable paddle assembly, the closure is shown attached to a complementary stirring vessel shown in cross section.

Referring now to the drawings, FIG. 1 reveals a magnetic stirring apparatus including a stirring vessel closure body 2 coupled with a stirring vessel 4. A paddle assembly 6 is suspended from closure body 2 and is adjustably positioned within vessel 4 at a selected height, or elevation. Paddles 8 an 10 preferably extend substantially perpendicularly outward from paddle assembly 6 to stir vessel contents such as cells and growing medium.

Closure body 2 is shown as being of a generally conical shape having a sloped facing 12 with access ports 14 and 16 extending outwardly therefrom. Optional internally threaded sealing caps 18 and 20 are installed on exteriorly threaded ports 14 and 16. Elevation screw cap 22 is positioned directly atop closure body 2. Inside of peripheral portion 24 of closure body 2 engages with the top of vessel 4 to provide a fluid seal to prevent cells or growing medium from escaping from stirring vessel 4 and prevents contaminants from entering vessel 4.

Contents placed within vessel 4 are stirred by paddles 8 and 10 as a result of bringing the vessel into close proximity of rotating magnetic fields such as those generated by stirring plates typically used in laboratories (not shown in the drawings). The rotating magnetic field causes magnet 26, shown being perpendicular to paddles 8 and 10 in FIG. 1, to spin about the vertical axis of the paddle assembly which causes the paddles to spin likewise. Stirring plates typically have an adjustable speed control circuit for controlling the speed in which the magnetic field rotates and hence the speed at which the paddle assembly will rotate.

Figure 2:
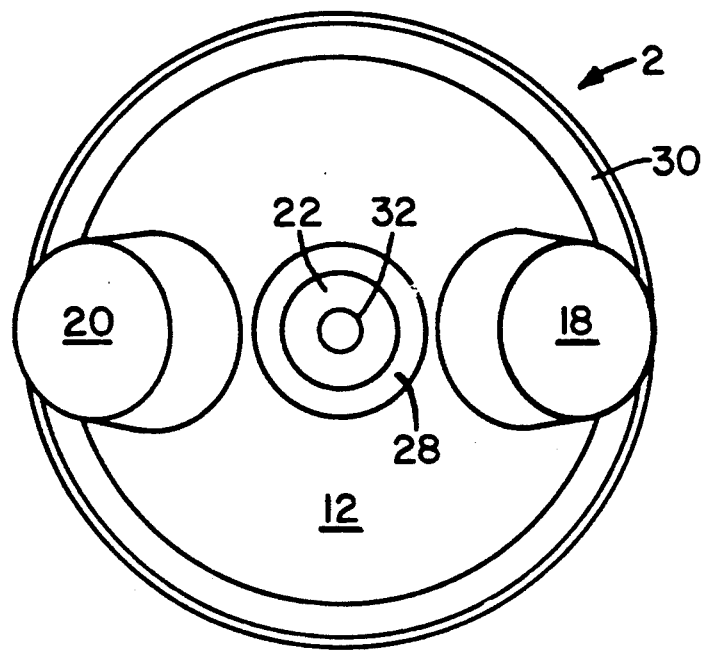
FIG. 2 is a top view of an embodiment of the disclosed magnetic stirring vessel closure.

A top view of closure body 2 having the generally conical shape as shown in FIG. 1 is shown in FIG. 2.

Closure body 2 has a substantially horizontal facing 28 located below elevation screw cap 22. Horizontal facing 28 joins sloped facing 12 which in turn joins with annular facing 30. Peripheral skirt portion 24, shown in FIG. 1, extends vertically downward from underneath annular ring 30. An opening covered by a permeable membrane 32 for allowing the exchange of gases within vessel 4 and the ambient may be included in the top of elevation screw cap 22. The path in which gases will be able to travel to and from the ambient via membrane 32 will become apparent in the remaining drawings.

Figure 3:
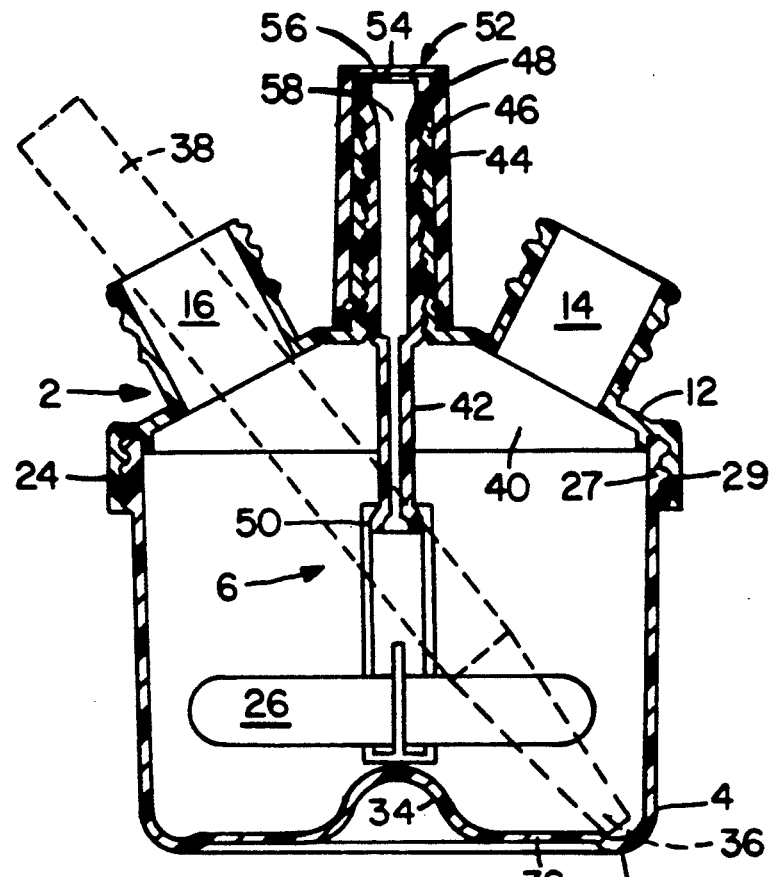
FIG. 3 is a cross-sectional view of the embodiment of the disclosed magnetic stirring vessel closure and stirring vessel shown in FIG. 1.

A cross-sectional front view of the magnetic stirring apparatus as illustrated in FIG. 1 is shown in FIG. 3. Open ended stirring vessel 4 is provided with means for releasably coupling with closure body 2. The coupling means used in the embodiment of FIG. 3 uses screw threads 27 about the opening of vessel 4 which coact with threads 29 about the inside of peripheral skirt portion 24 of closure body 2. However, other coupling means can be utilized in lieu thereof. The outside of peripheral skirt portion 24 may include knurling, ribs, or other textured surfaces to enhance hand gripping of closure body 2.

Stirring vessel 4 includes bottom 32 having a centrally located raised dimple 34. Dimple 34 prevents the contents of the vessel undergoing stirring from accumulating into the region directly below the paddle assembly where agitation is minimal or nonexistent. Radiused trough 35 extends downward from the lower periphery of vessel 4 to slightly raise bottom 32 and to provide a stable footing for vessel 4. By radiusing and extending trough 35 in such a manner, vessel 4 may easily be removed from flat wet surfaces in which an undesired hydraulic seal may otherwise form if bottom 32 were not so raised by trough 35. Additionally, trough 35, upon rotating vessel 4 slightly by hand, provides a convenient area in which to pipette culture or liquids from the bottom of the vessel. Stirring vessel 4 may be made of glass, plastic material such polypropylene, or any other suitable material. Stirring vessel 4 preferably has a volume within the range of 50 to 2000 milliliters.

Figure 4:
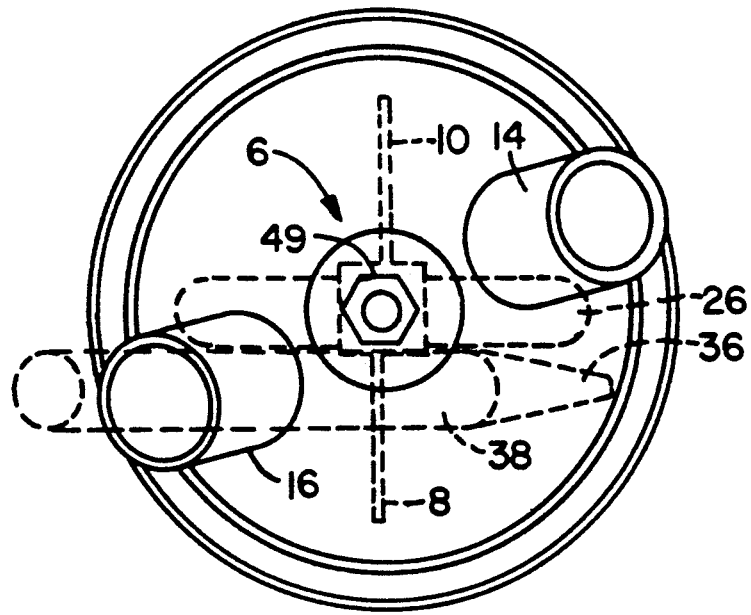
FIG. 4 is a top view of the closure and vessel shown in FIG. 3 showing, in phantom, the insertion of an instrument through an access port of the disclosed closure and reaching into a remote portion of the stirring vessel.

Closure body 2 has access ports 14 and 16 preferably extending generally perpendicularly from sloped facing 12. Sloped facing 12 is sloped at an angle from horizontal to allow instruments such as pipettes to pass by paddle assembly 6 and reach adjacent regions of stirring vessels having preselected depths. Sloped facing 12 preferably has an inclination within the range of 15° to 45° from horizontal or within the range of 50° to 80° from horizontal. A preferred angle of 27 degrees and 30 minutes from horizontal has been found particularly suitable for angling sloped facing 12. An illustration of such an insertion of a pipette through closure body 2 is shown in FIGS. 3 and 4. Pipette 38, shown in phantom, is inserted through a selected access port and into a vessel such as vessel 4. Tip 36 of pipette 38 is shown reaching into the bottom of a vessel and into trough 35. Thus, the dimensions of the access ports and the angles in which the access ports extend from closure body 2 may be selected to optimize instrument accessibility to regions within various vessels, including vessel 4. Preferably the access ports are sized and configured to extend a short horizontal distance, if any, past the side walls of stirring vessel 4, or any other vessel, in which the disclosed stirring vessel closure is attached. Therefore, by placing access ports on closure body 2, in lieu of placing them on the stirring vessel, as taught by prior art, the disclosed apparatus and vessels utilizing embodiments of the disclosed closure, may be packed more closely together.

FIG. 4 illustrates an embodiment of the present invention wherein the center line of a port and the center line of the closure body are nonplanar. Angling the orientation of the ports in this way allows a pipette or other instrument to be inserted into a stirring vessel without being blocked by the paddle assembly or stirring magnet.

Turning to FIG. 3 of the drawings, the generally conical shape of closure body 2 formed by horizontal facing 28, sloped facing 12, and annular facing 30, not only provides a means for angling access ports 14 and 16, but also provides a volumetric cavity 40 above vessel 4. Volumetic cavity 40 may be sized relative to the volume of vessel 4 to provide a desired ratio of the volume of air to the volume of growing medium contained within vessel 4. A ratio of 1 to 1 has been found to provide favorable results for cultures typically stirred and cultivated within magnetic stirring vessels.

Closure body 2 may be made of plastic materials such as polypropylene, or any other suitable material.

Paddle assembly 6 is suspended above dimple 34 of vessel 4 by a hollow elevation screw 42. Elevation screw 42 has an externally threaded upper portion 44 which is threadingly received by an open ended elevation screw hub 46 surrounding an opening in horizontal facing 28 and extending upwardly therefrom. Upper portion 44 terminates into an outwardly flared end 48. Elevation screw 42 has a shaft extending downward and terminating into an outwardly flared lower bearing surface 50. Lower bearing surface 50 is sized to pass through elevation screw hub 46 and is configured to provide a bearing surface in which paddle assembly 6 may be rotated about.

Upper end 48 of elevation screw 42 is shaped to engage a removable elevation screw cap 52 which can be press fitted about upper end 48. Upper end 48 and screw cap 52 engage each other so that when screw cap 52 is rotated, elevation screw 42 is likewise rotated and is threaded into, or out of, elevation screw hub 46 depending on the direction in which the cap is rotated. FIG. 4 shows upper end 48 of elevation screw 42 shaped into an hexagonal nut 49 in which the inside of screw cap 52 has a complimentary hexagonal shaped recess to receive upper end 48 having hexagonal nut 49. Returning to FIG. 3, by rotating elevation screw 42, the elevation, or height, in which paddle assembly 6 is suspended from the bottom of a stirring vessel, may be selected. The limits of the elevation, or height, adjustment of paddle assembly 6 is determined by the length of elevation screw 42. Specifically, when upper flared end 48 rests against screw hub 46, paddle assembly 6 will be at its lowermost elevation and when paddle assembly rests against closure body 2, paddle assembly 6 will be at its upper most elevation.

An O-ring 106, or other sealing means, may be disposed between elevation screw cap 52 and elevation screw hub 46 in order to provide a seal between the inside of screw cap and the hub.

Elevation screw cap 52 may have an opening 54 in the end that is covered by a porous membrane 56 if so desired. Upon positioning screw cap 52 onto elevation screw 42, membrane 56 will be positioned against upper end 48 of elevation screw 42 and proximate to passage 58 which extends through elevation screw 42. Paddle assembly 6 is designed not to block passage 58, therefore passage 58 provides a path in which gases may be exchanged between the interior of vessel 4 and the ambient.

Figure 5:
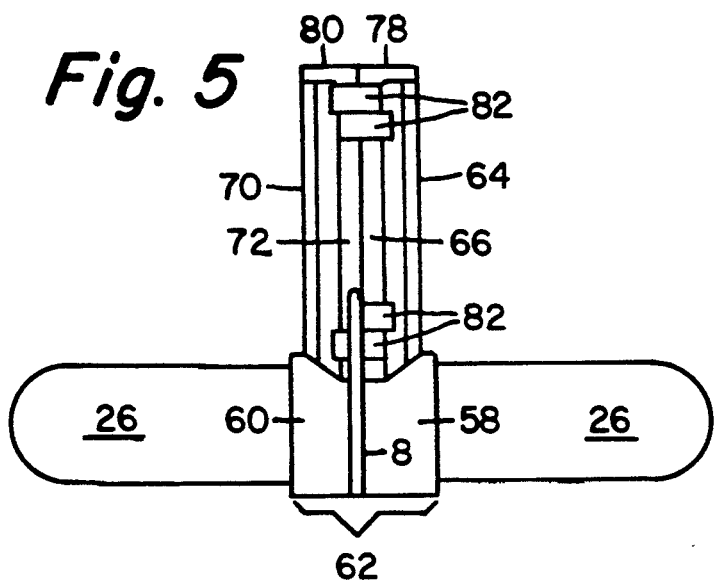
FIG. 5 is front view of an embodiment of the disclosed paddle assembly.

FIG. 5 shows paddle assembly 6 in isolation from the stirring apparatus shown in preceding drawings. Paddle assembly 6 is formed by combining hollow sleeve components 59 and 60. The sleeves form a magnet retaining end 62 wherein removable stirring magnets 26 are fittable therein. Sleeves 59 and 60 each have a plurality of respective vertical members 64, 66, 68 (68 not shown in FIG. 5), and 70, 72, 74 (74 not shown in FIG. 5). The vertical members extend upward from the sleeves and terminate into respective C-shaped bearing surfaces 78 and 80 configured to be mounted about lower bearing surface 50 of elevation screw 42. Securing tabs 82, are mounted on adjacent vertical members and interlock with the adjacent vertical members to provide means for securing the combinable sleeve components of paddle assembly 6 together. To remove paddle assembly 6 from elevation screw 42, securing tabs 82 are pried away from their respective interlocked positions, and bearing surface 78 and 80 separate allowing the components of paddle assembly 6 to be removed from elevation screw 42.

Figure 6:
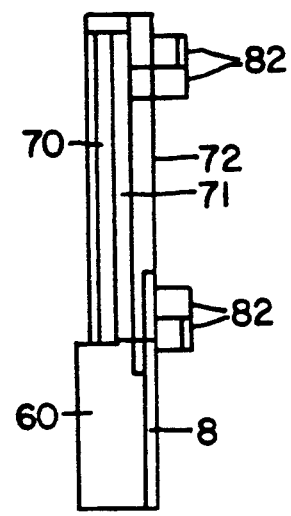
FIG. 6 is a front view of one of the combinable components of the disclosed paddle assembly shown in FIG. 5.

A side view of one component of paddle assembly 6 is shown in FIG. 6. The component includes sleeve 60 having paddle 8 extending therefrom and vertical members 70 and 72 having securing tabs 82 in view. There is an open region 71 between vertical members 70 and 72 which provides a path in which gases may be travel into and through passage 58 of elevation screw 42 for venting purposes described above. Such open regions are present between other adjacent vertical members as well.

Figure 7:
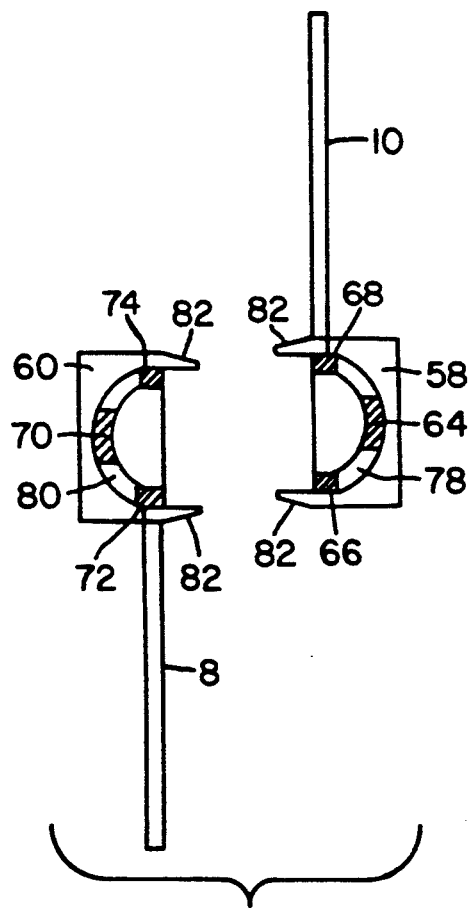
FIG. 7 is a top view of two combinable components of the disclosed paddle assembly shown in FIG. 6.

An exploded top view of the combinable components of paddle assembly 6 is shown in FIG. 7. Vertical members 64, 66, 68, 70, 72, and 74 are shown in phantom below C-shaped bearing surfaces 78 and 80. Hollow sleeves 59 and 60 each have a paddle 10, and 8 respectively, extending perpendicularly therefrom. However, it is not necessary for each sleeve to have a paddle extending therefrom as a single sleeve could have a paddle extending from both sides thereof. Furthermore the paddles need not be perpendicular to each sleeve.

Figure 8:
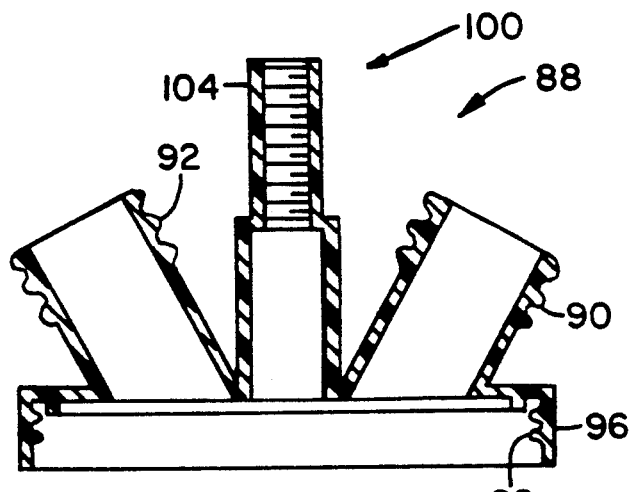
FIG. 8 is a cross-sectional side view of an alternative embodiment of the disclosed magnetic stirring vessel closure.

An alternative embodiment of the invention is shown in FIG. 8. FIG. 8 is a cross-sectional view of a stirring vessel closure body 88 that may be used in lieu of closure body 2 previously described. Closure body 88 may be made of a plastic material such as polypropylene, or any other suitable material. Closure body 88 has angled access ports 90 and 92 extending from a substantially horizontal facing 94. An angle of 62 degrees and 30 minutes from horizontal has been found to be particularly suitable for angled access ports 90 and 92. Horizontal facing 94 joins outer peripheral skirt portion 96 which extends substantially vertically downward from horizontal facing 94. The peripheral skirt portion includes a threaded region 98, or other means for coupling with stirring vessels. The exterior of peripheral skirt portion 96 may also include knurling, raised ribs, or other such surfaces to enhance hand gripping thereabout.

A hollow elevation screw hub 100 surrounds an opening in horizontal facing 94 and extends upward from horizontal facing 94. Elevation screw hub 100 has a lower section 102 which is of a slightly larger inside and outside diameter than the remainder upper portion 104 of hub 100. A hub step 108 provides a transition between upper and lower portions of hub 100. The interior of upper portion 104 of hub 100 is threaded for receiving elevation screw 42 described herein.

As with closure 2, an O-ring 106, or other sealing means, may be disposed between the inside of a previously described elevation screw cap and the exterior of screw hub 100 to form a seal therebetween.

The operation of closure 88 is the same as closure 2, with the exception that there is no longer a conically shaped open region such as volumetric cavity 40 within closure body 2. However, skirt portion 96 may be vertically extended to provide a volumetric cavity within closure 88 if desired.

When paddle assembly 6 is raised by rotating elevation screw 42, the portions of vertical members 66–74 including bearing surfaces 78 and 80, will ultimately come to rest within the larger diameter lower section 102 as transition step 108 will prevent bearing members 78 and 80 from traveling further upward.

Although detailed descriptions of preferred embodiments of the invention have been disclosed herein, it will be apparent to those skilled in the art that various modifications and dimensional changes can be made thereto without departing from the spirit and scope of the invention as set forth in the following claims.

We claim:

1. A magnetic stirring vessel closure for use with a paddle assembly comprising:
   a) a closure body having a circular and substantially horizontal facing having a centrally located aperture surrounded by a hollow internally threaded elevation screw hub extending upward from the horizontal facing;
   the closure body further having an annular, intermediately located, and sloped facing connecting the horizontal facing to an outwardly located annular facing, the outwardly located annular facing having a peripheral skirt portion extending substantially vertically downward therefrom, the peripheral skirt portion having means to couple with stirring vessels;
   the sloped intermediate facing having an aperture and at least one open-ended access port outwardly extending from said aperture;
   b) an externally threaded elevation screw sized and configured to be threadingly received by the elevation screw hub, the elevation screw having a downwardly extending shaft terminating into an outwardly flared lower end sized to pass through the screw hub and configured to provide an annular bearing surface for the paddle assembly, the elevation screw further having an upper outwardly flared end; and
   c) an elevation screw cap removably fitted about the upper outwardly flared end of said elevation screw.

2. A paddle assembly for use with the stirring vessel closure of claim 1 wherein the paddle assembly comprises a plurality of combinable hollow sleeves, which sleeves combine to form means for retaining a magnet, the sleeves having a plurality of vertical members extending upward therefrom, the vertical members terminating into a plurality of coacting bearing surfaces configured to encompass and ride about the annular bearing surface of the elevation screw, one or more of the hollow sleeves having a paddle extending outwardly therefrom, and means for releasably securing the hollow sleeves together being mounted on adjacent vertical members.

3. The stirring vessel closure of claim 1 further comprising an access port closure cap having sealing means to seal at least one access port and retention means for retaining the cap upon said at least one access port.

4. The stirring vessel closure of claim 1 wherein the elevation screw has a passage extending axially therethrough and the elevation screw cap has a gas permeable membrane positioned proximate to the upper end of the elevation screw.

5. The stirring vessel closure of claim 1 further comprising a sealing means disposed between the elevation screw cap and the elevation screw hub.

6. The stirring apparatus of claim 1 wherein the sloped intermediate facing is inclined in the range of 15 to 45 degrees from horizontal and said at least one access port extends substantially perpendicularly from the intermediate facing.

7. A magnetic stirring apparatus comprising:
   a) a stirring vessel having side walls joined to a bottom having a centrally located upwardly extending dimple, the bottom being radiused to form a circumferential trough where the sidewalls meet the bottom;
   b) a closure body having a circular and substantially horizontal facing having a centrally located aperture surrounded by a hollow internally threaded elevation screw hub extending upward from the horizontal facing;
   the closure body further having a annular, intermediately located, and sloped facing connecting the horizontal facing to an outwardly located annular facing, the outwardly located annular facing having a peripheral skirt portion extending substantially vertically downward therefrom, the peripheral skirt portion having means to couple with the stirring vessel;
   the sloped intermediate facing having an aperture and at least one open-ended access port outwardly extending from said;
   c) an externally threaded elevation screw sized and configured to be threadingly received by the elevation screw hub, the elevation screw having a downwardly extending shaft terminating into an outwardly flared lower end sized to pass through the screw hub and configured to provide an annular bearing surface, the elevation screw further having an upper outwardly flared end;
   d) an elevation screw cap removably fitted about the upper outwardly flared end of said elevation screw; and
   e) a paddle assembly having a plurality of combinable hollow sleeves, which sleeves combine to form means for retaining a magnet, the sleeves having a plurality of vertical members extending upward therefrom, the vertical members terminating into a plurality of coacting bearing surfaces configured to encompass and ride about the annular bearing surface of the elevation screw, one or more of the hollow sleeves having a paddle extending outwardly therefrom, and means for releasably securing the hollow sleeves together being mounted on adjacent vertical members.

8. The stirring apparatus of claim 7 wherein the sloped intermediate facing is inclined in the range from 50 to 80 degrees from horizontal and said at least one access port extends substantially perpendicularly from the intermediate facing.

9. The stirring apparatus of claim 7 further comprising an access port closure cap having sealing means to seal at least one access port and retention means for retaining the cap upon said at least one access port.

10. The stirring apparatus of claim 7 wherein the elevation screw has a passage extending axially therethrough and the elevation screw cap has a gas permeable membrane positioned proximate to the upper end of the elevation screw.

11. The stirring apparatus of claim 7 further comprising a sealing means disposed between the elevation screw cap and the elevation screw hub.

12. The stirring apparatus of claim 7 wherein the stirring vessel and the closure body are made of plastic materials.

13. The stirring apparatus of claim 7 wherein the stirring vessel has a volume within the range of 50 to 2000 milliliters.

14. A magnetic stirring vessel closure for use with a paddle assembly comprising:
 a) a closure body having a circular and substantially horizontal facing having an aperture surrounded by a hollow internally threaded elevation screw hub extending upward from the horizontal facing;
 the closure body further having an outer peripheral portion extending substantially vertically downward from the horizontal facing, the peripheral portion having means to couple with stirring vessels;
 the horizontal facing having at least one additional aperture surrounded by an open-ended access port, the access port extending at an angle to the horizontal facing;
 b) an externally threaded elevation screw sized and configured to be threadingly received by the elevation screw hub, the elevation screw having a downwardly extending shaft terminating into an outwardly flared lower end sized to pass through the screw hub and configured to provide an annular bearing surface for the paddle assembly, the elevation screw further having an upper outwardly flared end;
 c) an elevation screw cap removably fitted about the upper outwardly flared end of said elevation screw.

15. A paddle assembly for use with the stirring vessel closure of claim 14 wherein the paddle assembly comprises a plurality of combinable hollow sleeves, which sleeves combine to form means for retaining a magnet, the sleeves having a plurality of vertical members extending upward therefrom, the vertical members terminating into a plurality of coacting bearing surfaces configured to encompass and ride about the annular bearing surface of the elevation screw, one or more of the hollow sleeves having a paddle extending outwardly therefrom, and means for releasably securing the hollow sleeves together being mounted on adjacent vertical members.

16. A magnetic stirring vessel closure with an elevation-adjustable paddle assembly comprising:
 a) a closure body having a circular and substantially horizontal facing having an centrally located aperture surrounded by a hollow internally threaded elevation screw hub extending upward from the horizontal facing;
 the closure body further having an annular, intermediately located facing connecting the horizontal facing to an outwardly located annular facing, the outwardly located annular facing having a peripheral skirt portion extending substantially vertically downward therefrom, the peripheral skirt portion having means to couple with stirring vessels;
 the intermediate facing having an aperture and at least one open-ended access port outwardly extending from said aperture in the intermediate facing and extending at an angle to the horizontal facing;
 b) an externally threaded elevation screw sized and configured to be threadingly received by the elevation screw hub, the elevation screw having a downwardly extending shaft terminating into an outwardly flared lower end sized to pass through the screw hub and configured to provide an annular bearing surface for the paddle assembly, the elevation screw further having an upper outwardly flared end; and
 c) an elevation screw cap removably fitted about the upper outwardly flared end of said elevation screw.

17. The stirring vessel closure of claim 16, wherein the center line of said at least one access port and the center line of the closure body are nonplanar.

18. The stirring vessel closure of claim 17, wherein the at least one open-ended outwardly extending access port extends radially no further than the peripheral skirt portion.

19. The stirring vessel closure of claim 17, wherein the intermediate facing is sloped.

20. The stirring vessel closure of claim 17, wherein the intermediate facing is substantially horizontal.

* * * * *